United States Patent
Thibeault (10) Patent No.: US 9,468,552 B2
(45) Date of Patent: Oct. 18, 2016

(54) BACK BRACE

(71) Applicant: Scott M. Thibeault, Durham, NC (US)

(72) Inventor: Scott M. Thibeault, Durham, NC (US)

(*) Notice: Subject to any disclaimer, the term of this patent is extended or adjusted under 35 U.S.C. 154(b) by 351 days.

(21) Appl. No.: 13/758,224

(22) Filed: Feb. 4, 2013

(65) Prior Publication Data

US 2014/0221890 A1    Aug. 7, 2014

(51) Int. Cl.
     *A61F 5/01*          (2006.01)
     *A61F 5/02*          (2006.01)

(52) U.S. Cl.
     CPC .................. *A61F 5/012* (2013.01); *A61F 5/02* (2013.01); *A61F 5/022* (2013.01); *A61F 5/024* (2013.01); *A61F 5/026* (2013.01); *A61F 5/028* (2013.01)

(58) Field of Classification Search
     CPC ............ A61F 5/01; A61F 5/012; A61F 5/02; A61F 5/022; A61F 5/024; A61F 5/026; A61F 5/028
     USPC ................ 602/13, 14, 19; 2/44, 267, DIG. 3
     See application file for complete search history.

(56) References Cited

U.S. PATENT DOCUMENTS

| | | | | |
|---|---|---|---|---|
| 4,682,587 | A * | 7/1987 | Curlee ........................... | 602/13 |
| 5,449,341 | A * | 9/1995 | Harris ............................ | 602/63 |
| 5,451,200 | A * | 9/1995 | LaBella et al. ................. | 602/19 |
| 7,276,037 | B2 * | 10/2007 | Ravikumar .................... | 602/13 |
| 8,012,112 | B2 * | 9/2011 | Barberio ........................ | 602/14 |
| 2006/0287625 | A1 * | 12/2006 | Rauch ............................ | 602/19 |
| 2013/0053739 | A1 * | 2/2013 | Mustafa ......................... | 602/13 |
| 2014/0012171 | A1 * | 1/2014 | Brown et al. .................. | 602/13 |

* cited by examiner

*Primary Examiner* — Alireza Nia
*Assistant Examiner* — Keri J Nelson
(74) *Attorney, Agent, or Firm* — Banner & Witcoff, Ltd.

(57) ABSTRACT

A back brace includes an inner frame member having an interior surface, an exterior surface, a plurality of recesses formed in the interior surface, and a clamshell shape configured to wrap around a portion of a torso of a user. Each of a plurality of inserts is positioned in one of the recesses. An inflatable bladder is positioned on the exterior surface of the inner frame member, and an exterior shell member is wrapped about the bladder and the inner frame member.

21 Claims, 9 Drawing Sheets

BACK BRACE

FIELD

Aspects of this invention relate generally to a back brace and, in particular, to a back brace having one or more inflatable bladders on an exterior surface of an inner frame member.

BACKGROUND

Back braces are well known for treating patients with various spinal abnormalities characterized as Scoliosis. Many back braces deal with a specific section of the spine, while some braces attempt to treat multiple zones. Known back braces include the Boston Brace, the Milwaukee Brace, the Cheneau Brace, and the Cheneau Light Brace.

Problems with known braces include friction, lack of breathability, and lack of flexibility. One of the major issues with known back braces is the rate of compliance. Because the braces are cumbersome and not comfortable, and because they may require assistance for the user to don the brace, users often fail to wear the brace for the full amount of time prescribed by medical professionals.

It would be desirable to provide a back brace that reduces or overcomes some or all of the difficulties inherent in prior known devices. Particular advantages will be apparent to those skilled in the art, that is, those who are knowledgeable or experienced in this field of technology, in view of the following disclosure of the invention and detailed description of certain embodiments.

SUMMARY

The principles of the invention may be used to provide a back brace that is easy to use, is more comfortable to wear, has the required firm support while allowing for a soft fit, eliminates bulk, and improves flexibility. In accordance with a first aspect, a back brace includes an inner frame member having an interior surface, an exterior surface, a plurality of recesses formed in the interior surface, and a clamshell shape configured to wrap around a portion of a torso of a user. Each of a plurality of inserts is positioned in one of the recesses. An inflatable bladder is positioned on the exterior surface of the inner frame member, and an exterior shell member is wrapped about the bladder and the inner frame member.

In accordance with another aspect, a back brace includes an inner frame member having an interior surface, an exterior surface, a plurality of recesses formed in the interior surface, and a clamshell shape and configured to wrap across a back of a torso of a user and around to a front of the torso of the user. Each of a plurality of inserts is positioned in one of the recesses. A plurality of bladders are positioned on the exterior surface of the inner frame member. Each bladder includes an inflation valve, and a pressure adjustment assembly configured to allow deflation of the bladder and to control a pressure of the bladder. An exterior shell member formed of a substantially non-stretchable material is wrapped about the bladder and the inner frame member, and includes a fastener.

In accordance with a further aspect, a back brace includes an inner frame member having an interior surface, an exterior surface, a plurality of recesses formed in the interior surface, and a clamshell shape defining a first arm and a second arm and configured to extend across a back of the user's torso. The first arm is configured to extend around a right side of the user to a front of the user's torso, and the second arm is configured to extend around a left side of the user to the front of the user's torso. Each of a plurality of inserts is positioned in one of the recesses and extends outwardly beyond the interior surface of the inner frame member. Each of a plurality of bladders is positioned on the exterior surface of the inner frame member. Each of a plurality of inflation valves is a check valve and is connected to one of the bladders. Each of a plurality of pressure adjustment assemblies is connected to one of the bladders and configured to allow deflation of the bladder and to control a pressure of the bladder. An exterior shell member is formed of a substantially non-stretchable material, is wrapped about the bladder and the inner frame member, and includes a zipper.

By providing a brace with an inner frame member and one or more adjustable bladders on an exterior of the inner frame member, the patient's experience wearing a brace can be improved, increasing the likelihood that the patient wears the brace when they should and, therefore, reducing the length of time they are required to wear the brace. These and additional features and advantages disclosed here will be further understood from the following detailed disclosure of certain embodiments.

The figures referred to above are not drawn necessarily to scale, should be understood to provide a representation of particular embodiments of the invention, and are merely conceptual in nature and illustrative of the principles involved. Some features of the back brace have been enlarged or distorted relative to others to facilitate explanation and understanding. The same reference numbers are used in the drawings for similar or identical components and features shown in various alternative embodiments. Back braces as disclosed herein would have configurations and components determined, in part, by the intended application and environment in which they are used.

DETAILED DESCRIPTION OF CERTAIN PREFERRED EMBODIMENTS

Figure 1:
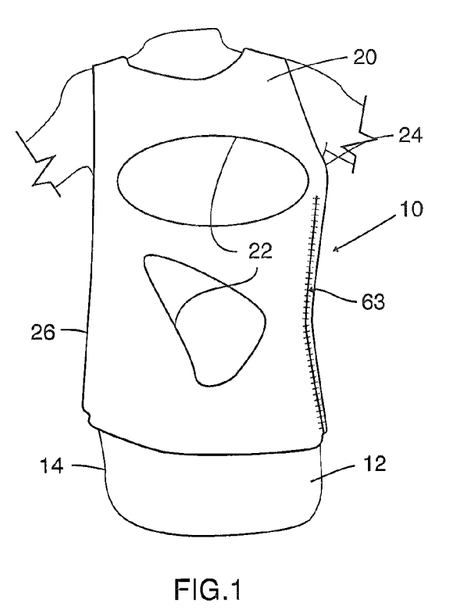
FIG. 1 is a front elevation view of a brace shown on a torso of a user.
Figure 2:
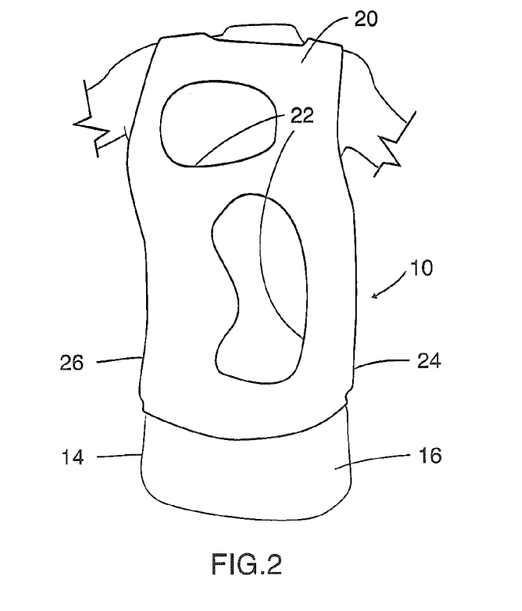
FIG. 2 is a rear elevation view of the brace of FIG. 1.

A back brace 10 is depicted in FIG. 1 in use on a front 12 of a torso 14 of a user, and in FIG. 2 on a back 16 of torso 14. Back brace 10 includes an inner frame member 18 (Seen in FIGS. 3-6) covered by an exterior shell member 20. Exterior shell member 20 may include a plurality of cutouts 22. Cutouts 22 may be positioned at locations on torso 14 opposite areas on torso 14 where pressure is applied by brace 10, thereby allowing the user's spine to move.

As illustrated here, back brace 10 is shown in use on a female torso 14, with one of the cutouts 22 positioned about the breasts of the user. It is to be appreciated that back brace 10 can be used on both female and male torsos, and that cutouts 22 could be positioned at any desired locations. The specific locations of cutouts 22 will be determined, at least in part, by the design of the brace 10, the condition of the user, and their treatment plan. It is to be appreciated that any number of cutouts 22 can be formed in exterior shell member 20 and that, in certain embodiments, exterior shell member can be provided without any cutouts 22 at all.

As seen in FIGS. 3-6 inner frame member 18 has a clamshell shape and is configured to wrap around torso 14 of the user. Specifically, inner frame member 18 extends across back 16 of the user and around the left side 24 and right side 26 of torso 14 to front 12. By using such a clamshell configuration, the user can put on brace 10 by themself, free of any external fasteners. This simplifies donning of brace 10, as well as increasing comfort, and improving performance of brace 10, all of which enhance compliance of the user.

Inner frame member 18 is designed and manufactured to meet the specific alignment needs of the user and, therefore, is customized to match the particular configuration of the user's torso. In certain embodiments, to form inner frame member 18, a scan of the user's torso is conducted, providing a 3D image of the user's torso. Using the 3D image, a template representing the user's torso is then milled from a block of foam, providing the base upon which inner frame member 18 is formed. A sheet of material is then vacuum formed over the template, resulting in an inner frame member 18 that is shaped to conform to the specific contours of the user's torso.

In certain embodiments, inner frame member 18 is formed modified polyethylene, providing a soft comfortable feel to the touch, while still providing strength and flexibility. Inner frame member 18 is designed to be sufficiently flexible enough for the user to don the brace themself, while at the same time being rigid enough to maintain its shape on the user's torso. Other suitable materials for inner frame member 18 will become readily apparent to those skilled in the art, given the benefit of this disclosure.

Figure 3:
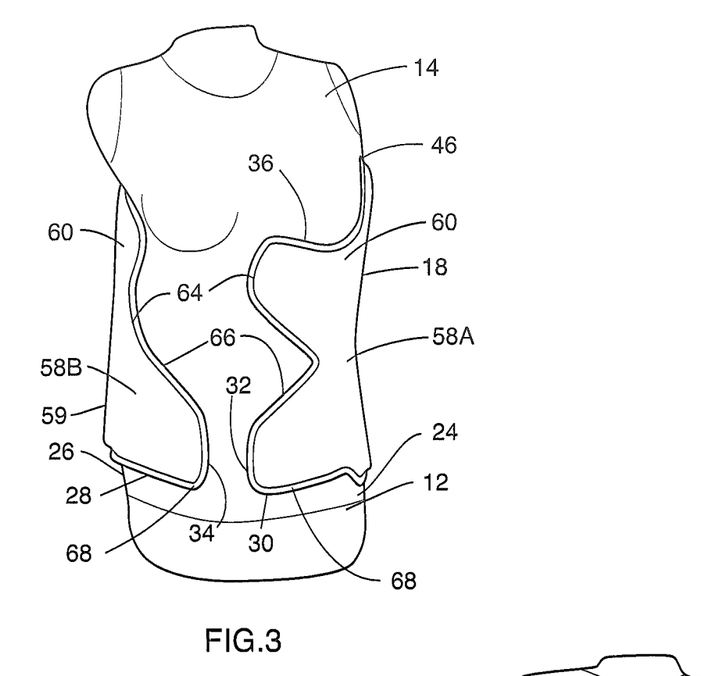
FIG. 3 is a front elevation view of an inner frame member and bladders of the brace of FIG. 1.

Inner frame member 18 has a plurality of arms that extend in different directions to provide support, leverage, and correction for the user, depending on their specific needs. In the illustrated embodiment, as seen in FIG. 3, inner frame member 18 includes a first arm 28 that extends laterally around right side 26 of the torso 14 and across a portion of front 12 of torso 14. A second arm 30 extends laterally around left side 24 of torso 14 across a portion of front 12 of torso 14 such that an outermost end 32 of second arm 30 is opposed to and spaced from an outermost end 34 of first arm 28. A third arm 36 extends laterally around left side 28 of torso 14 across a portion of front 12 of torso 14 above second arm 30. An outermost end 38 of third arm 36 is positioned above and spaced from outermost end 32 of second arm 30.

A fourth arm 40 extends from left side 24 upwardly and to the right along a portion of the right side of back 16 of torso 14. A fifth arm 42 extends from right side 26 upwardly and to the left along a portion of the right side of back 16 of torso 14, above and spaced from an outermost end 44 of fourth arm 40. A sixth arm 46 extends from third arm 36 upwardly along left side 24 of torso 14 and toward back 16.

The arms of inner frame member 18 are positioned to provide corrective alignment for a specific user's spine. Thus, it is to be appreciated that the number, location, and orientation of the arms of inner frame member 18 will depend on the severity and configuration of the deformation of the user's spine, and the treatment plan recommended by a doctor or other health professional.

Figure 7:
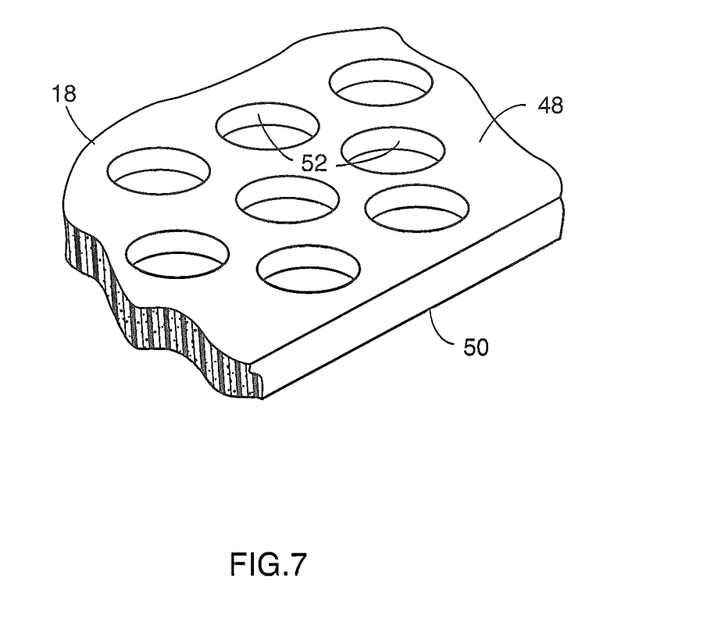
FIG. 7 is a perspective view, shown partially broken away, of an interior surface of the inner frame member of the brace of FIG. 1.
Figure 8:
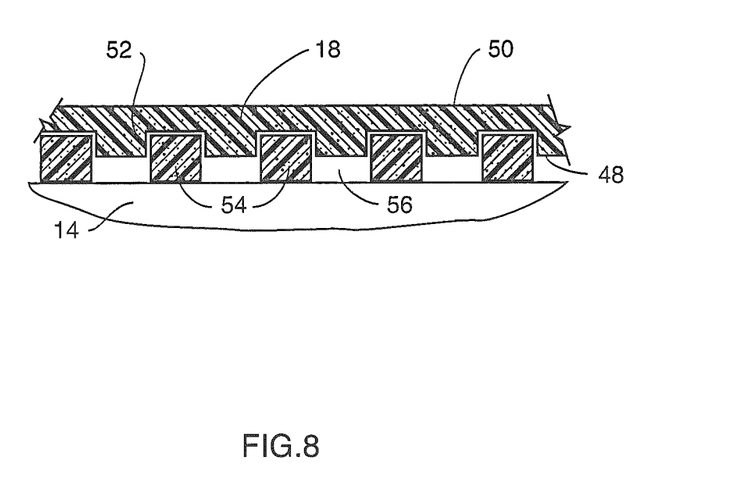
FIG. 8 is a section view of the inner frame member of the brace of FIG. 1, shown with inserts positioned within recesses in the inner frame member.

As illustrated in FIGS. 7-8, inner frame member 18 has an interior surface 48 and an exterior surface 50. A plurality of recesses 52 may be formed in interior surface 48. Inserts 54 are positioned within corresponding recesses 52. Inserts 54 extend outwardly beyond interior surface 48 such that a gap or chamber 56 is formed between interior surface 48 and torso 14, thereby providing ventilation for the user. Such ventilation reduces discomfort to the user when wearing brace 10, thereby increasing the likelihood of the user keeping brace 10 on.

In certain embodiments, recesses 52 may be formed when the sheet of material used to form inner frame member 18 is vacuum formed on the template of the user's torso. To do so, a plurality of projections are created on the exterior surface of the template when it is milled from the block of foam. When the sheet of material is vacuum formed, the projections on the template create corresponding recesses 52 on interior surface 48 of inner frame member 18. Other means of forming recesses 52 in inner frame member 18 will become readily apparent to those skilled in the art, given the benefit of this disclosure.

In certain embodiments, inserts 54 are formed of a closed cell foam material that provides superior impact absorption properties and resistance to the absorption of liquids. In some embodiments, inserts 54 can be formed of a closed cell cross-linked polyethylene. Inserts 54 may be secured within recesses 52 with an adhesive. Other means of securing inserts 54 within recesses 52 will become readily apparent to those skilled in the art, given the benefit of this disclosure.

As illustrated in FIGS. 7-8, inserts 54 are cylindrical members. It is to be appreciated that inserts 54 can have any desired shape, and that other possible shapes will become readily apparent to those skilled in the art, given the benefit of this disclosure.

Recesses 52 and corresponding inserts 54 can be positioned at any location along interior surface 48 of inner frame member 18. In certain embodiments, substantially the entire interior surface 48 could be covered with an array of recesses 52 and corresponding inserts 54. In other embodiments, recesses 52 and inserts 54 may be positioned only within a select number of discrete locations. For example, recesses and inserts 54 may be positioned at any location where corrective engagement of brace 10 with the user's torso is required.

One or more inflatable bladders 58 are positioned on exterior surface 50 of inner frame member 18. Bladders 58 are formed by securing a film or sheet of material 59 to exterior surface 50 of inner frame member 18, thereby defining bladder 58 between sheet 59 and inner frame member 18. In certain embodiments, bladders 58 are formed of a sheet of polyurethane, providing a thin, light, translucent material that is strong and prevents absorption. Such a material allows sheet 59 to be easily manipulated and shaped to conform to the complex shape of inner frame member 18, which matches that of the user's torso. Other suitable materials for sheet 59 will become readily apparent to those skilled in the art, given the benefit of this disclosure.

In certain embodiments, sheet 59 is UV welded to inner frame member 18. It is to be appreciated that sheet 59 may be RF welded to exterior surface 50 of inner frame member 18. Other means of securing sheet 59 to inner frame member 18 will become readily apparent to those skilled in the art, given the benefit of this disclosure.

Inflatable bladders 58 have an exterior surface 60, and an interior surface 62, and are configured to provide specific, measured amounts of pressure to select targeted areas of back brace 10. By applying pressure through bladders 58 in selected locations, back brace 10 serves to help re-align the user's spine. Since each user's condition is unique to that individual, the location and configuration of bladders 58 and the arms of inner frame member 18 are designed to treat the condition of the user's spine. Brace 10 wraps around torso 14 from back 16 to front 12 in order for the applied forces to use the bones of the user, including the pelvis, for example, as a base to spring from, thereby providing the required leverage to affect the user's spine.

After bladders 58 are secured to inner frame member 18, inner frame member 18 is ready to be positioned on the user's torso. After inner frame member 18 is positioned on the user, exterior shell member 20 can be pulled on or put on to cover inner frame member 18 and bladders 58. Once exterior shell 20 is positioned over inner frame member 18 and bladders 58, bladders 58 are inflated.

Exterior shell member 20 may include a fastener 63, such as a zipper as seen in FIG. 1, allowing it to be opened to facilitate pulling it over inner frame member 18 and bladders 58. Exterior shell member 20 serves to confine bladders 58 on inner frame member 18, and turn the force of expansion from bladders 58 back onto inner frame member 18 and the user's torso. In certain embodiments, exterior shell member 20 is formed of a no-stretch material, such as 100% cotton. In addition to helping contain the forces of expansion, such a material provides a comfortable soft exterior surface for back brace 10, providing another reason for increased compliance.

In the embodiment shown here, there are two bladders 58 secured to inner frame member 18.

Figure 4:
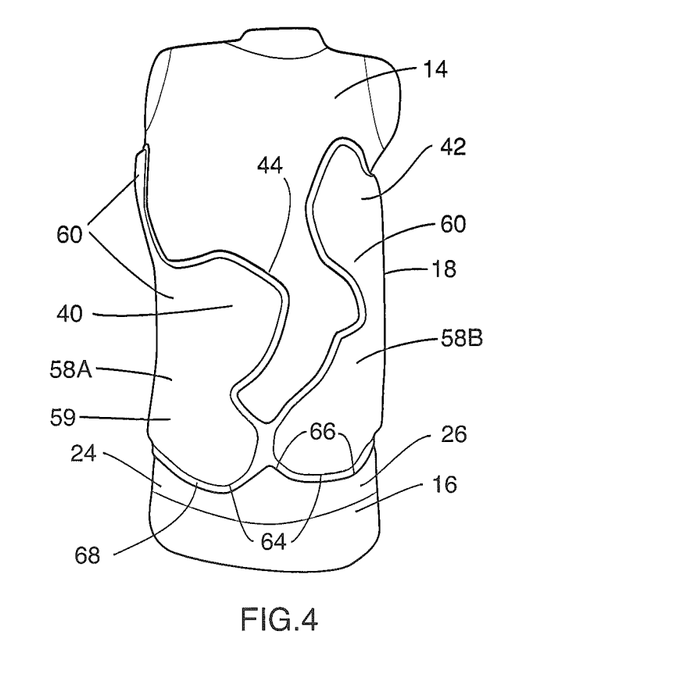
FIG. 4 is a back elevation view of an inner frame member and bladders of the brace of FIG. 1.
Figure 5:
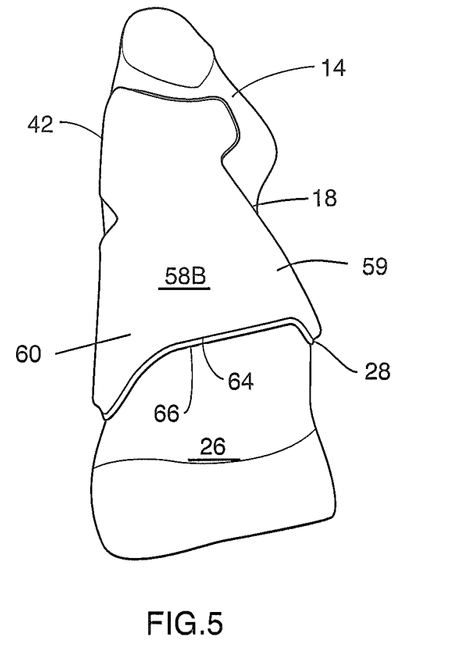
FIG. 5 is a right side elevation view of an inner frame member and bladders of the brace of FIG. 1.
Figure 6:
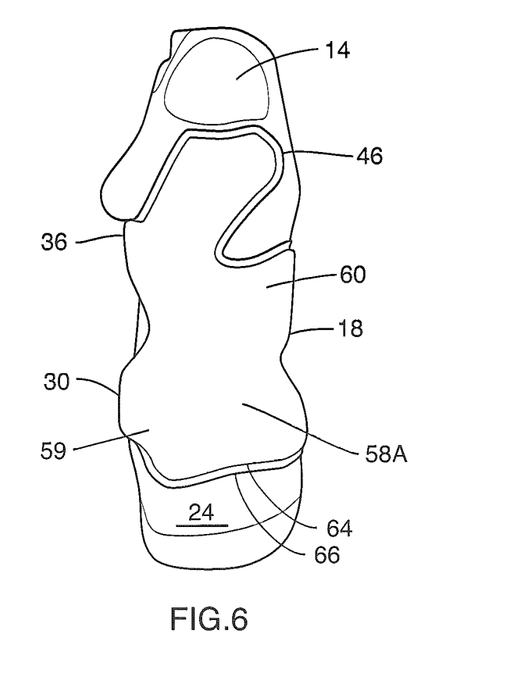
FIG. 6 is a left side elevation view of an inner frame member and bladders of the brace of FIG. 1.

As seen in FIGS. 3-6, a first bladder 58A extends from back 16 of inner frame member 18, up along fourth arm 40, around left side 24, and along each of second arm 30, third arm 36, and sixth arm 46. A second bladder 58B extends from back 16 upwardly along fifth arm 42, around right side 26, and along first arm 28. As can be seen in FIG. 4, first bladder 58A is spaced from second bladder 58B in the middle of the back of inner frame member 18.

It is to be appreciated that more than two bladders 58 can be provided on inner frame member 18, and that, in certain embodiments, a single bladder 58 could be provided on inner frame member 18. The number, location, and configuration of bladder(s) 58 will be determined based on a recommended treatment plan for the user.

Bladders 58 are positioned on inner frame member 18 such that a peripheral edge 64 of each bladder 58 is spaced inwardly from a peripheral edge 66 of inner frame member 18 to provide a flange or apron 68 extending about the periphery of inner frame member 18. Apron 68 allows the peripheral edge of inner frame member 18 to better mold and adapt to the contours of the user's torso. In certain embodiments, peripheral edge 64 of each bladder 58 is spaced inwardly from peripheral edge 66 of inner frame member 18 by between approximately 0.25 and approximately 0.4 inches.

Figure 9:
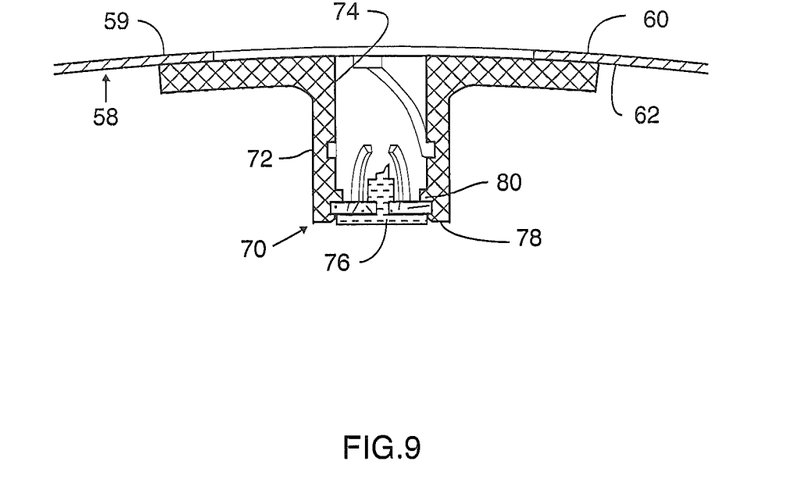
FIG. 9 is a section view of an inflation valve of a bladder of the brace of FIG. 1.
Figure 10:
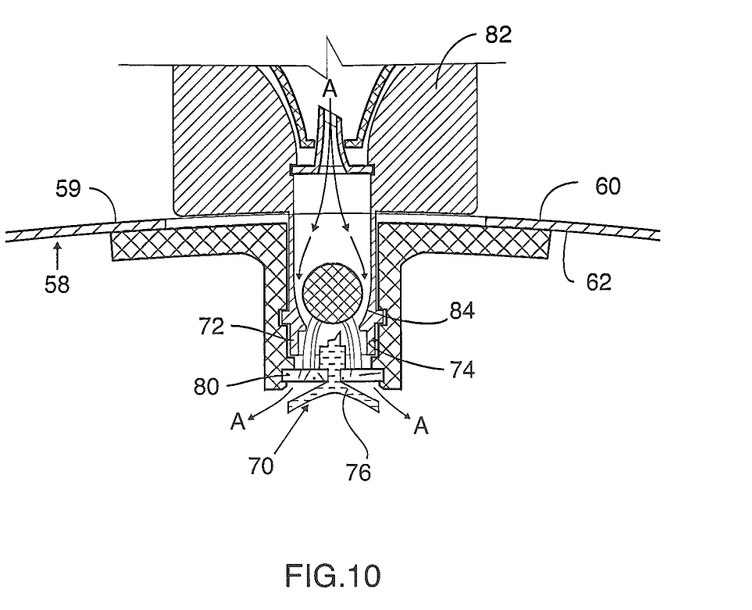
FIG. 10 is a section view of the inflation valve of FIG. 9, shown with a fluid supply source connected to the inflation valve.

Bladder 58 is designed to be inflated and deflated by the user and/or a doctor, therapist or other medical professional. For inflation, bladder 58 includes an inflation valve 70, as illustrated in FIG. 9-10, secured to interior surface 62 of bladder 58. In certain embodiments, inflation valve 70 is secured to bladder 58 by ultrasonic or RF welding. Other means for securing inflation valve 70 to bladder 58 will become readily apparent to those skilled in the art, given the benefit of this disclosure.

Inflation valve 70 may be a one-way check valve only allowing inflation of bladder 58. In the embodiment illustrated in FIGS. 9-10, inflation valve 70 includes a housing 72 with an aperture 74 extending therethrough. A disc 76 is seated at an inner most end of aperture 74. Disc 76 is movable inwardly toward the interior of bladder 58 to allow fluid, such as compressed air or $CO_2$, for example, to flow into and inflate bladder 58. Disc 76 is seated against a shoulder 80 within aperture 74 to prevent flow of the fluid outwardly through aperture 74.

To inflate bladder 58, a fluid supply source 82 is attached to inflation valve 70 to insert fluid into bladder 58. In certain embodiments, fluid supply source 82 is a canister of compressed air or compressed $CO_2$. A nozzle 84 of fluid supply source 82 is inserted into aperture 74, and as the pressurized contents of fluid supply source 82 are released, disc 76 moves inwardly, allowing the fluid to move into bladder 58 as the arrows A indicate. In certain embodiments, fluid supply source 82 may be engaged and disengaged from aperture 74 with a quarter turn engagement mechanism in known fashion.

For deflation and adjustment of pressure within bladder 58, a pressure adjustment assembly 86 is provided on each bladder 58. As illustrated in FIGS. 11-14, pressure adjustment assembly 86 includes a housing 88 positioned within bladder 58, with its top surface 90 bonded or otherwise secured to interior surface 62 of bladder 58. A central aperture 92 extends through housing 88. A pair of 0-rings 94 are seated in corresponding grooves 96 formed in top surface 90.

Figure 11:
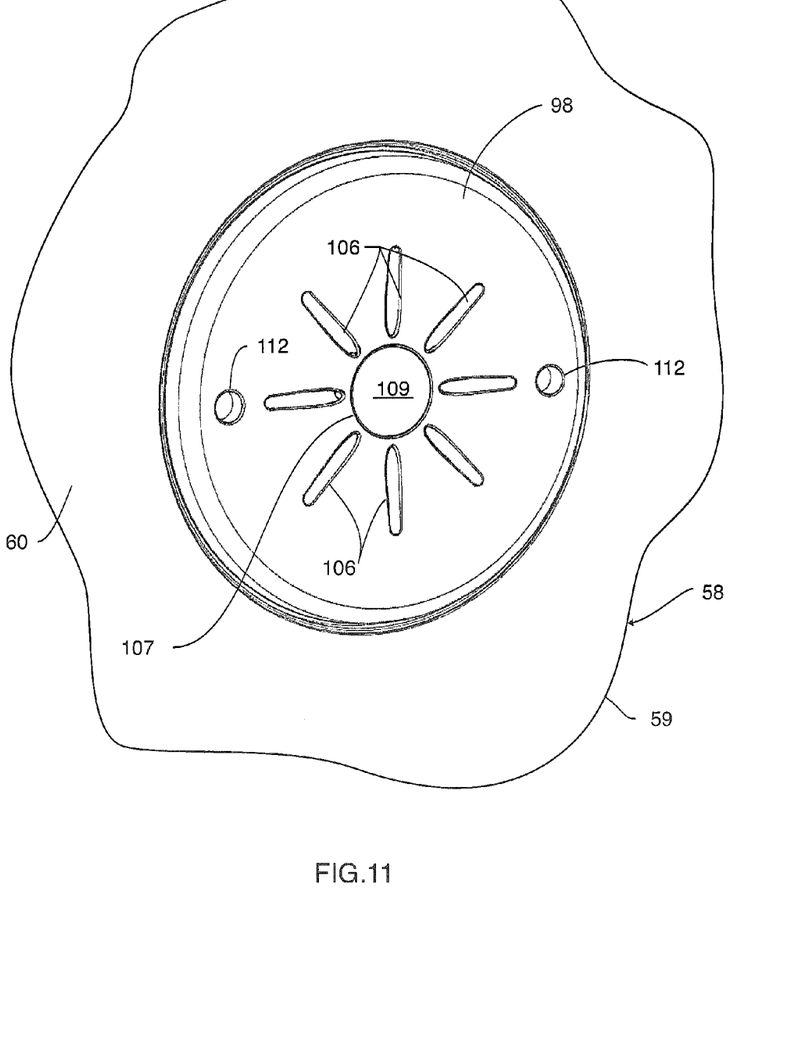
FIG. 11 is a perspective view of a pressure adjustment assembly of a bladder of the brace of FIG. 1.
Figure 12:
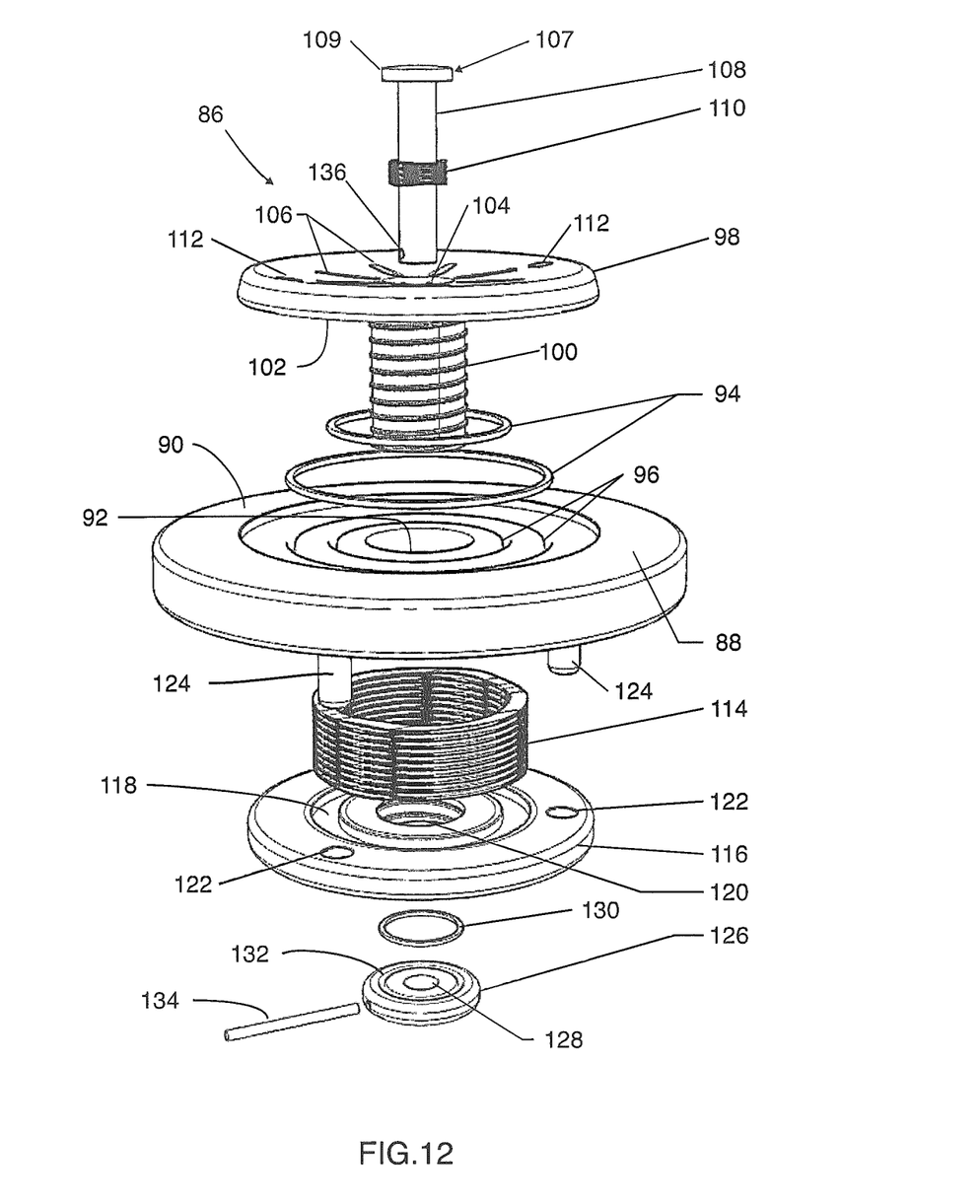
FIG. 12 is an exploded view of the pressure adjustment assembly of FIG. 11.

A control member 98 has a threaded projection 100 extending downwardly from its lower surface 102, with a central aperture 104 extending therethrough. A plurality of radially extending slits 106 are formed in control member 98, and are in fluid communication with central aperture 104. A plunger 107 having a plunger rod 108 and a plunger head 109 is received in central aperture 104. A plunger spring 110 surrounding plunger 108 urges plunger 108 upwardly away from control member 98. An opposed pair of apertures or recesses 112 is formed in the surface of control member 98 near its peripheral edge.

A control spring 114 is positioned below housing 88, and serves to determine the pressure at which pressure adjustment assembly 86 opens and fluid is released from bladder 58. A compression plate 116 is seated below control spring 114, and includes a groove 118 in which control spring 114 is seated. A threaded aperture 120 in compression plate 116 receives a lower end of threaded projection 100 of control member 98. Each of a plurality of apertures 122 in compression plate 116 receives a corresponding rod 124 extending downwardly from housing 88 so as to guide the movement of compression plate 116.

A plunger base plate 126 is positioned below compression plate 116, and has a central aperture 128 through which plunger rod 108 extends. An O-ring 130 is seated in a groove 132 formed in the upper surface of plunger base plate 126. A locking pin 134 extends through an aperture 136 formed in the lower end of plunger rod 108 to retain plunger rod 108 within pressure adjustment assembly 86.

Figure 13:
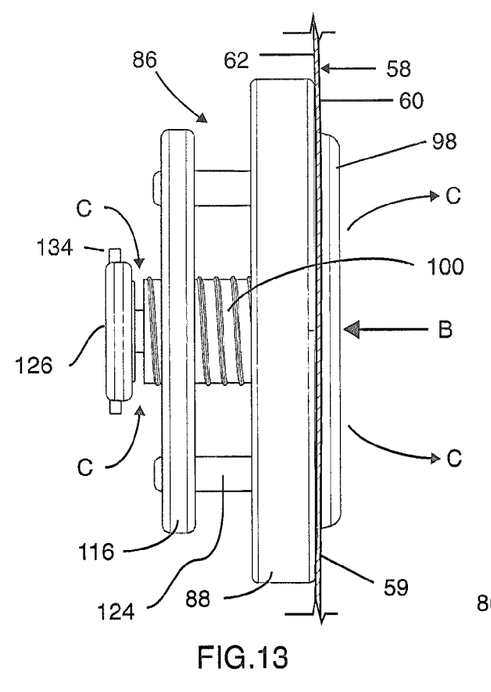
FIG. 13 is a side elevation view of the pressure adjustment assembly of FIG. 11, shown with its plunger depressed to deflate the bladder.

To manually release the fluid from bladder 58 with pressure adjustment assembly 86, plunger head 109 is depressed in the direction of arrow B, as seen in FIG. 13. Plunger base plate 126 is then moved downwardly away from compression plate 116, providing a path for fluid to escape from bladder 58 upwardly through threaded projection 100 and slots 106, as illustrated by arrows C.

Figure 14:
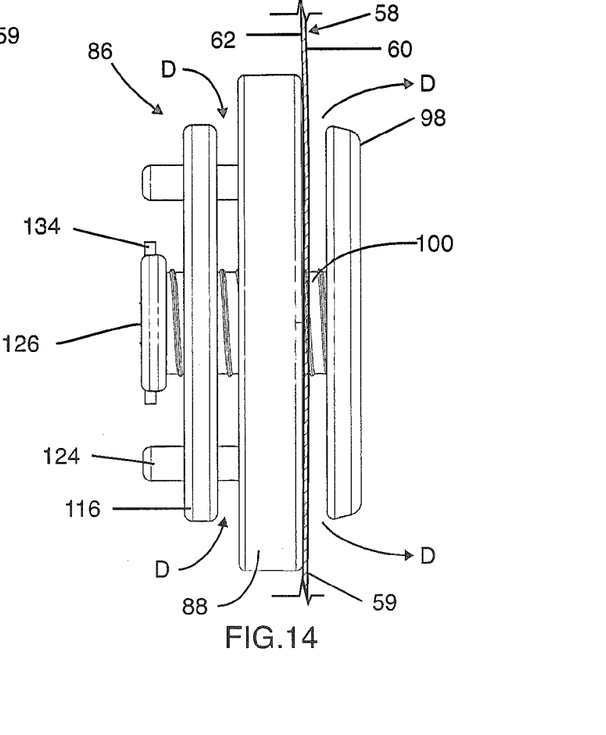
FIG. 14 is a side elevation view of the pressure adjustment assembly of FIG. 11, shown with the bladder exceeding the preset pressure and fluid exiting the bladder.

In operation, as illustrated in FIG. 14, if the pressure in bladder 58 exceeds the preset compression pressure of control spring 114, compression plate 116 moves upwardly, moving control member 98 away from housing 88, allowing fluid to escape from bladder 58 as shown by the arrows D.

The preset compression pressure of control spring 114 is adjusted by rotating control member 98 in a clockwise or counterclockwise direction, thereby adjusting the distance between compression plate 116 and housing 88, and compressing or expanding control spring 114.

Figure 15:
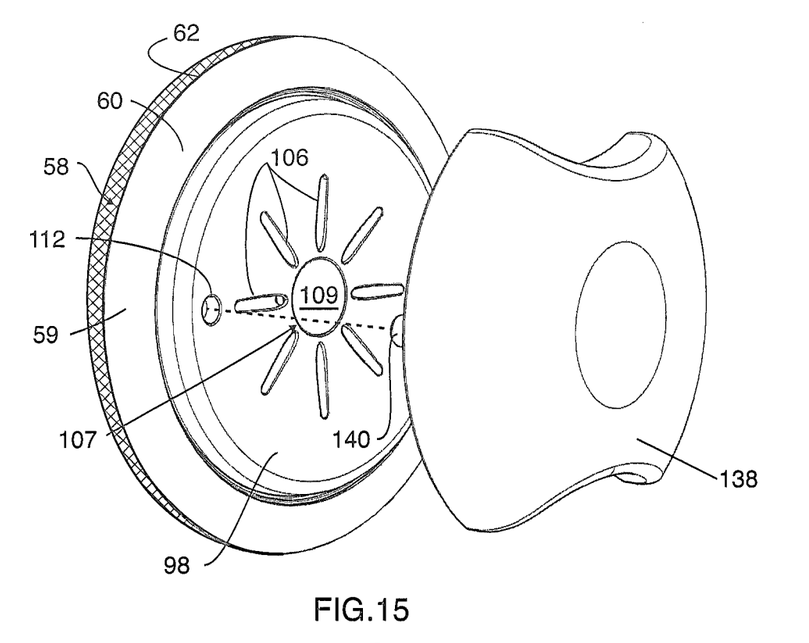
FIG. 15 is an exploded perspective view of the pressure adjustment assembly of FIG. 1 with its adjustment tool.
Figure 16:
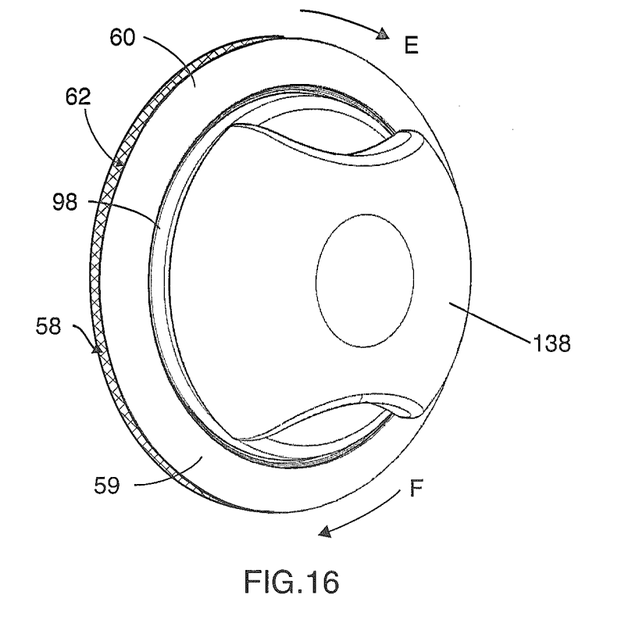
FIG. 16 is a perspective view of the pressure adjustment assembly of FIG. 1 with its adjustment tool.

As seen in FIGS. 15-16, a pressure adjustment tool 138 can be used to rotate control member 98 and adjust the preset compression pressure. Pins 140 that extend inwardly from the inner surface of pressure adjustment tool 138 are received in recesses 112 in control member 98 when pressure adjustment tool 138 is engaged with control member 98. Once they are engaged, the operator can twist adjustment tool 138 clockwise or counterclockwise as shown by arrows E and F, respectively, which will rotate control member 98, and set the desired pressure.

It is to be appreciated that pressure adjustment tool 138 can be removable, so that it can remain under control of the doctor, therapist or other medical individual in charge of the user's treatment regimen. This could reduce the likelihood of the pressure in the bladders 58 being altered by the user, which could negatively affect their treatment plan.

Thus, while there have been shown, described, and pointed out fundamental novel features of various embodiments, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is the intention, therefore, to be limited only as indicated by the scope of the claims appended hereto.

What is claimed is:

1. A back brace comprising:
    an inner frame member having an interior surface, an exterior surface, a plurality of recesses formed in the interior surface, and a clamshell shape configured to wrap around a back, sides, and a portion of a front of a torso of a user such that the inner frame member can be retained on the user's torso without any fasteners;
    a plurality of inserts, each insert positioned in one of the recesses;
    an inflatable bladder positioned on the exterior surface of the inner frame member; and
    an exterior shell member configured to be wrapped about the bladder and the inner frame member after the inner frame member has been wrapped around the user's torso.

2. The back brace of claim 1, wherein the exterior shell member is formed of a substantially non-stretchable material.

3. The back brace of claim 1, wherein the exterior shell member is formed of cotton.

4. The back brace of claim 1, wherein the exterior shell member includes a fastener.

5. The back brace of claim 4, wherein the fastener is a zipper.

6. The back brace of claim 1, further comprising at least one additional bladder positioned on the exterior surface of the inner frame member, each additional bladder including an inflation valve and a pressure adjustment assembly.

7. The back brace of claim 1, wherein the inner frame member is formed of plastic.

8. The back brace of claim 1, wherein the inner frame member is formed of polyethylene.

9. The back brace of claim 1, wherein the bladder is configured to be inflated and deflated.

10. The back brace of claim 1, wherein the inserts are formed of a closed cell foam material.

11. The back brace of claim 1, wherein the inserts project outwardly beyond the interior surface of the inner frame member.

12. The back brace of claim 1, further comprising an inflation valve and a pressure adjustment assembly connected to the bladder.

13. The back brace of claim 12, wherein the pressure adjustment assembly includes a removable pressure adjustment tool.

14. The back brace of claim 12, wherein the inflation valve is a check valve.

15. The back brace of claim 1, further including a plurality of arms, each arm configured to extending along a portion of the torso of the user.

16. The back brace of claim 1, wherein the inner frame member is configured to extend across a back of the user's torso and includes a first arm extending around a right side of the user to a front of the user's torso and a second arm extending around a left side of the user to the front of the user's torso.

17. The back brace of claim 16, further comprising a third arm extending around one of the left side and the right side of the user to the front of the user's torso.

18. A back brace comprising:
    an inner frame member having an interior surface, an exterior surface, a plurality of recesses formed in the interior surface, and a clamshell shape and configured to wrap across a back, around sides, and across a portion of a front of a torso of a user, the inner frame member configured to be retained on the user's torso without any fasteners;
    a plurality of inserts, each insert positioned in one of the recesses;
    a plurality of bladders positioned on the exterior surface of the inner frame member, each bladder including an inflation valve, and a pressure adjustment assembly configured to allow deflation of each bladder individually and to control a pressure of each bladder individually; and an exterior shell member formed of a substantially non-stretchable material configured to be wrapped about the plurality of bladders and the inner frame member after the inner frame member has been wrapped around the user's torso, and including a fastener.

19. The back brace of claim 18, wherein the inner frame member is configured to extend across a back of the user's torso and includes a first arm extending around a right side of the user to a front of the user's torso and a second arm extending around a left side of the user to the front of the user's torso.

20. The back brace of claim 18, wherein the inserts project outwardly beyond the interior surface of the inner frame member.

21. A back brace comprising:

an inner frame member having an interior surface, an exterior surface, a plurality of recesses formed in the interior surface, and a clamshell shape defining a first arm and a second arm and configured to extend across a back of the user's torso, the first arm configured to extend around a right side of the and across a portion of a front of the user's torso, and the second arm configured to extend around a left side of the and across a portion of the front of the user's torso, such that the inner frame member can be retained on the user's torso without any fasteners;

a plurality of inserts, each insert positioned in one of the recesses and extending outwardly beyond the interior surface of the inner frame member;

a plurality of bladders positioned on the exterior surface of the inner frame member;

a plurality of inflation valves, each inflation valve being a check valve and connected to one of the bladders;

a plurality of pressure adjustment assemblies, each pressure adjustment assembly connected to one of the bladders and configured to allow deflation of the bladder and to control a pressure of the bladder and an exterior shell member formed of a substantially non-stretchable material configured to be wrapped about the plurality of bladders and the inner frame member after the inner frame member has been wrapped around the user's torso, and including a zipper.

* * * * *